United States Patent
Danley et al.

(10) Patent No.: US 7,416,328 B2
(45) Date of Patent: Aug. 26, 2008

(54) SYSTEM AND METHOD FOR A THERMOGRAVIMETRIC ANALYZER HAVING IMPROVED DYNAMIC WEIGHT BASELINE

(75) Inventors: Robert L. Danley, Collingswood, NJ (US); John W. Schaefer, Wilmington, DE (US)

(73) Assignee: Waters Investments Limited, New Castle, DE (US)

( * ) Notice: Subject to any disclaimer, the term of this patent is extended or adjusted under 35 U.S.C. 154(b) by 0 days.

(21) Appl. No.: 11/317,050

(22) Filed: Dec. 27, 2005

(65) Prior Publication Data

US 2006/0140246 A1    Jun. 29, 2006

Related U.S. Application Data

(60) Provisional application No. 60/639,301, filed on Dec. 28, 2004.

(51) Int. Cl.
*G01N 25/00* (2006.01)
*G01K 13/00* (2006.01)

(52) U.S. Cl. .................... 374/14; 374/141; 374/208; 436/908; 236/44 C

(58) Field of Classification Search .............. 374/10–14, 374/45, 29, 33, 141, 142, 55; 436/908; 236/44 C
See application file for complete search history.

(56) References Cited

U.S. PATENT DOCUMENTS

| | | | | |
|---|---|---|---|---|
| 3,470,732 A | * | 10/1969 | Welhoelter et al. | 374/47 |
| 4,304,118 A | * | 12/1981 | Bartha et al. | 374/11 |
| 4,537,572 A | * | 8/1985 | Hill et al. | 432/55 |
| 4,596,470 A | * | 6/1986 | Park | 374/14 |
| 4,964,734 A | * | 10/1990 | Yoshida et al. | 374/14 |
| 5,055,264 A | * | 10/1991 | Czarnecki | 422/80 |
| 5,321,719 A | * | 6/1994 | Reed et al. | 374/14 |
| 5,493,078 A | * | 2/1996 | Uchiike | 177/212 |
| 5,499,532 A | * | 3/1996 | Kaiho et al. | 73/76 |
| 5,509,733 A | * | 4/1996 | Danley | 374/11 |
| 5,826,983 A | * | 10/1998 | Nakamura et al. | 374/14 |
| 5,983,711 A | * | 11/1999 | Pappas et al. | 73/76 |
| 6,268,570 B1 | * | 7/2001 | McLendon et al. | 177/1 |
| 6,302,577 B1 | * | 10/2001 | Jennings et al. | 374/14 |

(Continued)

FOREIGN PATENT DOCUMENTS

SU    572739 A    9/1977

(Continued)

*Primary Examiner*—Gail Verbitsky
(74) *Attorney, Agent, or Firm*—Aslan Baghdadi; Paul, Hastings, Janofsky & Walker LLP

(57) ABSTRACT

Systems and methods for minimizing extraneous forces and calculating corrected weights of samples based on buoyancy factors for a thermogravimetric analyzer (TGA). The TGA includes a balance chamber and a furnace configured to heat a sample. A null balance is provided in the balance chamber and is used to measure the sample weight change during heating. The furnace includes a cylinder open at the top to receive a sample. The bottom of the cylinder is closed except for a small hole that allows a thermocouple to pass through. An infrared heat source may be provided to heat the cylinder. The balance chamber can be thermally isolated from the furnace using an actively cooled plate and a system of heat shields disposed between the furnace and balance chamber. A thermocouple disk is further provided to limit gas flow in the furnace and increase reliability of sample weight measurements.

38 Claims, 9 Drawing Sheets

U.S. PATENT DOCUMENTS

| | | | |
|---|---|---|---|
| 6,336,741 B1 * | 1/2002 | Blaine | 374/14 |
| 6,347,884 B1 * | 2/2002 | Faure et al. | 374/45 |
| 6,871,998 B2 * | 3/2005 | Carter et al. | 374/14 |
| 7,048,435 B2 * | 5/2006 | Shdaimah et al. | 374/14 |
| 7,104,680 B2 * | 9/2006 | Nakamura | 374/55 |
| 2003/0007542 A1 * | 1/2003 | Peterman et al. | 374/14 |
| 2006/0120431 A1 * | 6/2006 | Monceau et al. | 370/14 |
| 2007/0298112 A1 * | 12/2007 | Axt et al. | 424/489 |

FOREIGN PATENT DOCUMENTS

SU     572739 A * 9/1977

* cited by examiner

SYSTEM AND METHOD FOR A THERMOGRAVIMETRIC ANALYZER HAVING IMPROVED DYNAMIC WEIGHT BASELINE

This application claims priority to U.S. Provisional Application No. 60/639,301 filed Dec. 28, 2004 entitled System and Method for a Thermogravimetric Analyzer Having Improved Dynamic Weight Baseline.

BACKGROUND

1. Field of the Invention

The present invention relates generally to improving weight measurements of thermogravimetric analyzers. More particularly, the present invention relates to improving weight measurements for vertical thermogravimetric analyzers with a balance positioned above the furnace.

2. Background of the Invention

Thermogravimetry is an analytical technique wherein a sample to be evaluated is subjected to a desired temperature program while its weight and temperature are measured. The weight change or the rate of weight change with respect to time or temperature may be displayed as a function of the measured temperature or of time and various evaluations may be performed. The weight curve versus temperature may be analyzed to determine the magnitude of weight changes that occur and the temperature or the range of temperatures at which they occur or other more sophisticated analyses may be performed such as those that determine the kinetics of the process responsible for the weight change.

A typical thermogravimetric analyzer (TGA) consists principally of a sensitive balance to weigh the sample dynamically and a furnace to heat the sample. TGAs are described, for example, in U.S. Pat. No. 5,165,792, which is incorporated by reference herein and attached as Exhibit 1. There are generally three configurations for TGAs: a horizontal furnace 901 with a balance 903 alongside the furnace, as shown in FIG. 9A, a vertical furnace 905 with the balance 903 below the furnace 905, as shown in FIG. 9B, or a vertical furnace 905 with the balance 903 above the furnace, as shown in FIG. 9C. In each of the configurations, a pan 907 is connected to the balance 903 by a support 909. In principle, any type of balance may be employed. However, the majority of TGAs use a null type balance that measures the force required to maintain the balance in an equilibrium position. (An overview of the different types of balances that may be employed in a TGA may be found in "Automatic and Recording Balances," Saul Gordon and Clement Campbell, Anal. Chem. 32(5) 271R-289R, 1960.)

A null balance comprises a drive system that applies force to the balance movement that supports the sample pan and tare pan or counterweight, a displacement sensor, and electronic control and measurement circuitry. These drive systems are typically electromagnetic drive systems. In operation, a force applied to the balance movement by the drive system maintains the balance in the equilibrium, or null position. The force applied by the drive system to maintain the null position is a measure of the sample weight. Changes in sample weight cause the balance to be displaced from the equilibrium position, the displacement is sensed by the sensor and the balance movement is returned to equilibrium by the drive system. Null balances are capable of sensing mass changes that are well below one microgram. Null balances are also robust and relatively inexpensive.

When attempting to make high sensitivity weight measurements a number of undesirable forces may act on the balance, sample, sample pan, and associated components of the weighing system. (Some of these undesirable forces are described in Ultra Micro Weight Determination in Controlled Environments, S. P. Wolsky and E. J. Zdanuk eds., 1969, Interscience, 39-46). For example, adsorption and desorption from the moving components of the balance may cause spurious weight changes. Temperature fluctuations within the balance may cause weight changes due to thermal expansion of the balance arms or may affect the strength of the field developed by permanent magnets in electromagnetic drive systems so equipped. Static electric charges may collect and act on the balance assembly, sample, and pan. Convection currents within the furnace or within the balance chamber may generate forces on the sample pan and associated components. Buoyancy forces that vary with changes in gas density act on the sample and pan within the furnace. Radiometric forces that result from thermomolecular flow may act on the balance components in regions where temperature gradients exist. This particular problem may be especially severe when operating under vacuum. The dynamic weight baseline performance of a TGA depends critically on minimizing or compensating for these undesirable forces or disturbances.

The dynamic weight baseline of a TGA is the weight measured when an experiment is performed without a sample. In principle, the dynamic weight measurement should be zero regardless of the temperature or the heating rate of the instrument. Deviations from zero are the result of disturbances acting on the balance assembly or pan. Given that a TGA is used to measure changes in weight that occur as a function of temperature or time, any weight change that occurs in the absence of a sample introduces uncertainty in the weight change measured during an experiment when a sample is present.

The choice of TGA configuration can affect the degree to which these extraneous forces act on the weight measurement. The horizontal configuration, as shown in FIG. 9A, is largely immune to convection currents and thermomolecular forces because they act on the weighing system orthogonally to the gravitational force acting on the sample and the balance. Horizontal systems, however, generally have much heavier balance components that act to reduce sensitivity. This is because the sample and its pan must be supported by a cantilever beam structure capable of resisting high temperatures within the furnace. The heavier structure requires a more robust suspension that can also reduce the balance sensitivity. Thermal expansion of the cantilever can materially affect the weight measurement, and although in principle it can be readily compensated for, thermal expansion remains a significant potential source of weighing errors.

Vertically arranged TGAs may have the balance below or above the furnace, as shown in FIGS. 9B and 9C. When the balance is below the furnace, as shown in FIG. 9B, the structure that supports the sample pan must be relatively massive because it supports the pan in compression and must resist the tendency to buckle, a tendency that is exacerbated by the high temperatures that are often achieved in TGA. Like the horizontal TGA, it requires a robust suspension and has relatively low sensitivity. However, it is easier to isolate the balance thermally from the furnace because hot gas and effluent from the furnace tend to rise because their temperature is high and density is low.

A TGA using a vertical furnace with the balance above it, as shown in FIG. 9C, offers the highest sensitivity because the mass of the pan suspension can be minimized, requiring only a fine filament to suspend the pan. This allows the mass of the balance and its suspension to be minimized. However, thermal isolation is more difficult because of the tendency of hot gas and effluents to rise. A vertical TGA is more susceptible to convection effects because of the orientation of the furnace and the relatively large vertical thermal gradients that accompany this configuration, and also because the thermomolecular forces act in parallel to the force of gravity and thus affect the weight measurement directly.

BRIEF SUMMARY OF THE INVENTION

The present invention relates to systems and methods for minimizing extraneous forces acting on the weighing system and calculating corrected weights of samples using buoyancy corrections. In an exemplary embodiment, a TGA includes a balance chamber and a furnace configured to heat a sample. A null balance is provided in the balance chamber and is used to measure the weight of the sample as it changes with temperature in the furnace. The furnace includes a cylinder that is open at the top to receive a sample. The bottom of the cylinder is closed except for a small hole that allows a thermocouple to pass through.

The thermocouple is part of a thermocouple assembly arranged in the cylinder. The thermocouple assembly includes a thermocouple attached to a disk that is substantially the same diameter as an inner diameter of the cylinder. In operation, the thermocouple assembly is arranged below the sample to limit convective flows around the sample, which could effect the weight measurement of the sample.

The TGA also includes a water-cooled plate between the balance chamber and the furnace. This helps to thermally isolate the balance chamber from the furnace. By thermally isolating the balance chamber, the balance temperature is kept constant, which eliminates weight errors that can result from thermal expansion of the balance beam and from changes in magnetic field strength due to changes of the magnet temperature. A thin metallic tube and system of heat shields are also used to isolate components of the balance from the heat of the furnace.

The TGA also includes a computer that can calculate a correction factor to be applied to the measured weight of the sample over various temperature ranges. The correction factors include a buoyancy factor for the apparatus, a buoyancy factor for the sample, or both. This correction is determined for the particular gas surrounding the sample. Once the correction factor is calculated, it can be applied to the measured sample weight to obtain a more accurate result.

In order to calculate a corrected sample weight, the TGA measures both the sample weight via the balance and the temperature of the sample via the thermocouple. Using these values, a correction factor, as described above, may be calculated and applied to the measured sample weight to get a corrected sample weight. In addition, in one embodiment of the present invention, a corrected temperature value is calculated that is used to determine the correction factor. This may be necessary, for example, at the beginning of an experiment when the gas in the furnace heats more quickly than the thermocouple, sample pan, and sample.

DETAILED DESCRIPTION OF THE INVENTION

The present invention relates to TGAs having an improved dynamic weight baseline. In a preferred embodiment of the present invention, the TGA configuration is vertical, with the balance mounted above the furnace. This preferred configuration provides the highest weight sensitivity.

Figure 1:
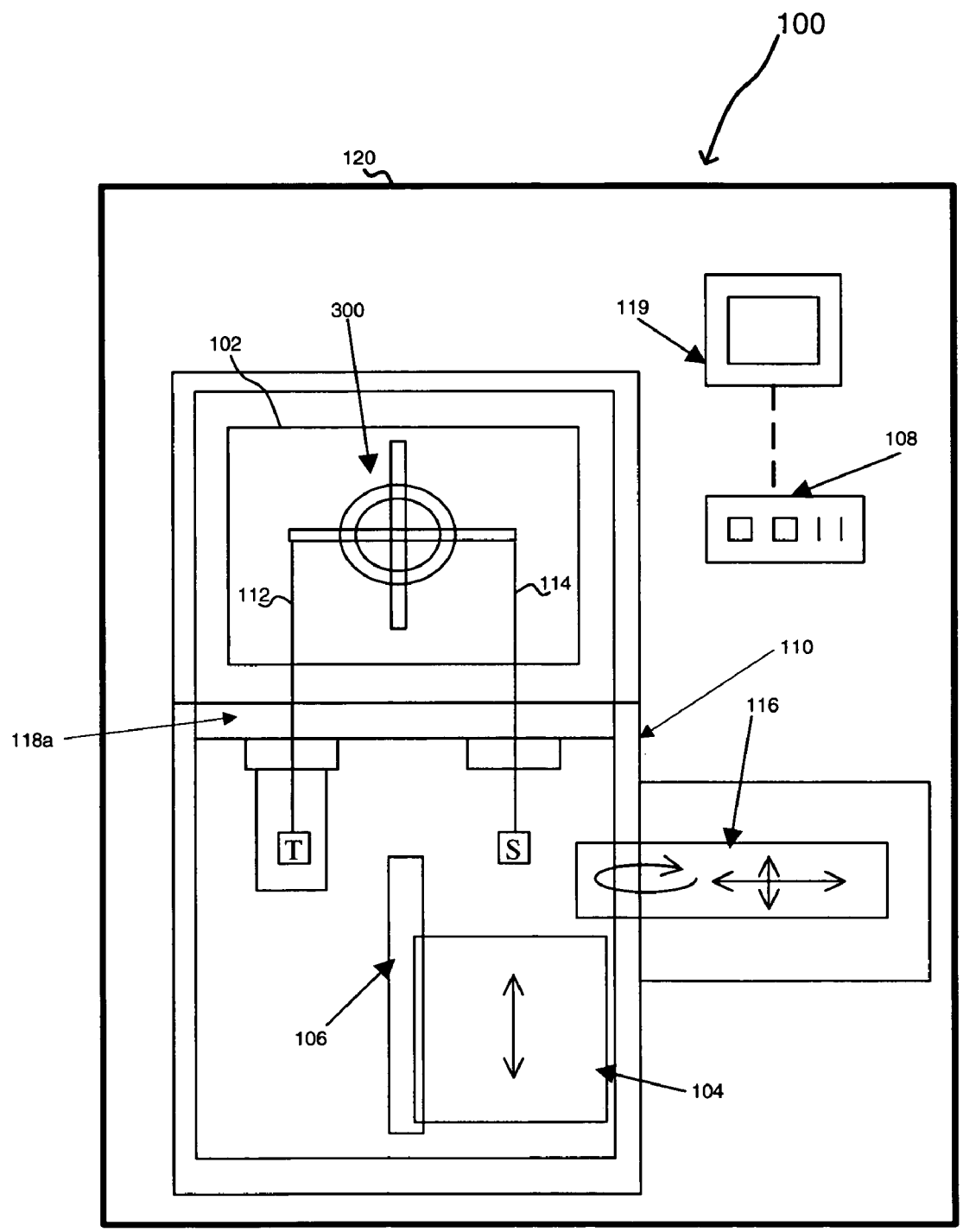
FIG. 1 is a schematic diagram showing a TGA in accordance with an exemplary embodiment of the present invention.

FIG. 1 is a schematic diagram of a TGA arranged in accordance with an exemplary embodiment of the present invention. TGA 100 includes a balance chamber 102, furnace 104, motorized linear actuator 106, electronic control unit 108, and TGA frame 110. Electronic control unit 108 may include a computer that controls the operation of TGA 100 and receives various measurements taken while TGA 100 is in use. For example, in one embodiment of the present invention control unit 108 controls furnace movement and heating, operation of autosampler 1116, and additionally manipulates measurement data taken to determine parameters such as sample temperature and sample weight, as described further below. In another embodiment of the present invention, control unit 18 can be configured to control operation of null balance 300.

A null balance 300 is arranged in balance chamber 102. Null balance 300 will be described in greater detail below. Attached to null balance 300 are suspension filaments (or "hang-down hooks") 112 and 114. Hang-down hook 112 supports tare pan T, hang-down hook 114 supports sample material S in a pan (not shown). Each of hang-down hooks 112 and 114 are formed of slender filaments. An autosampler 116 may be used to automatically load and unload sample materials in sample pans onto hang-down hook 114. It allows the TGA to perform a large number of experiments unattended. Autosampler 116 typically contains a tray capable of holding multiple sample pans and a mechanism for loading each pan in its turn on hang-down hook 114.

Figure 2:
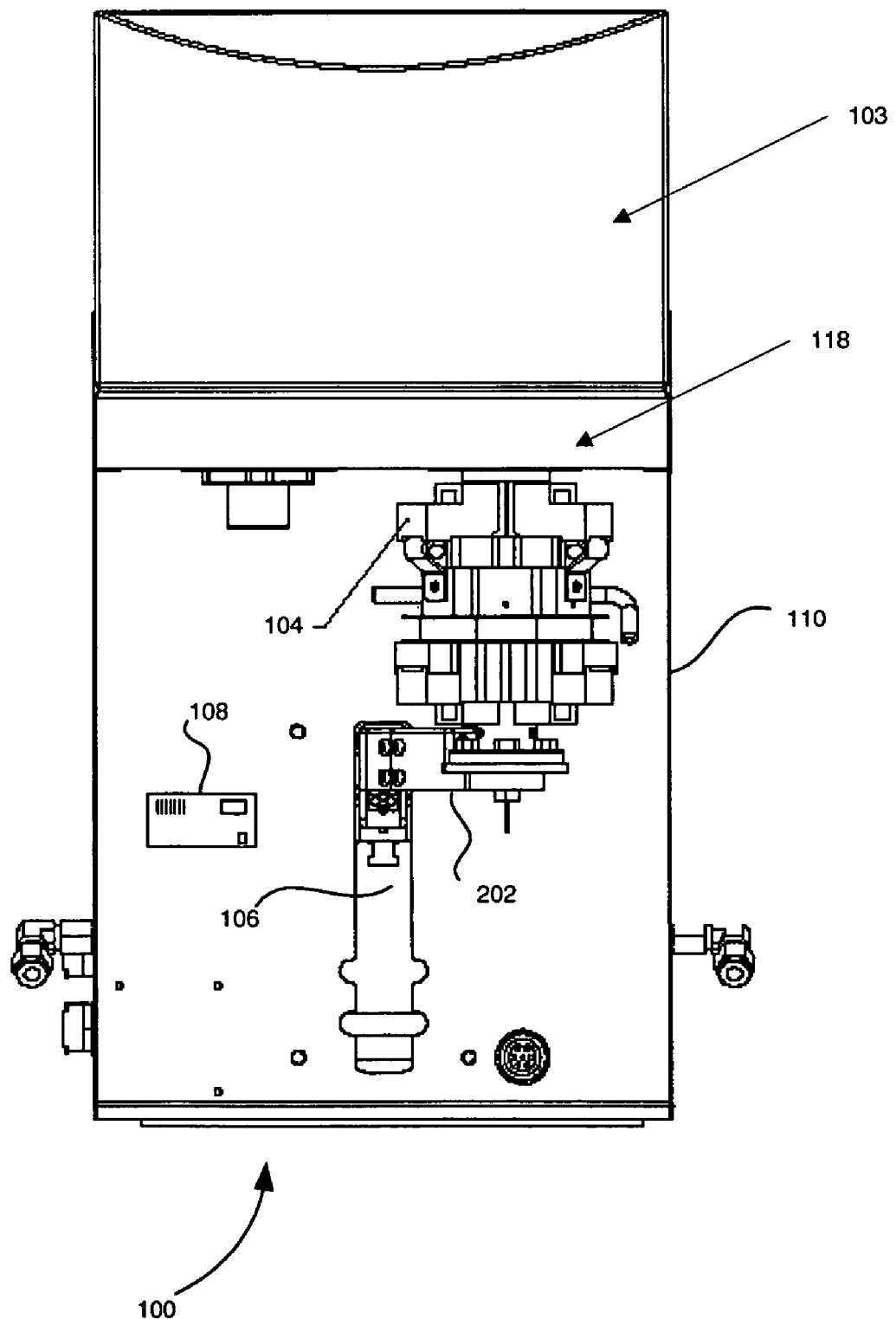
FIG. 2 is a schematic of a front view of the TGA shown in FIG. 1.

FIG. 2 illustrates further details of system 100 according to one embodiment of the present invention. Furnace 104 is attached to a support structure 202 (shown in FIG. 2), which is attached to motorized linear actuator 106. Motorized linear actuator 106 and electronic control unit 108 are mounted to TGA frame 110. Motorized linear actuator 106 is electrically connected (not shown) to electronic control unit 108. As shown in FIG. 1, furnace 104 is in the open position. In order to close the furnace, linear actuator 106 is engaged and moves furnace 104 upward to the closed position, as shown in FIG. 2.

An actively cooled plate 118 (see FIG. 2) located behind the indicated surface 118a, is arranged between balance chamber 102 and furnace 104. In this "actively cooled plate" generally refers to a plate that removes heat by circulating fluid such as water, but could also be a Peltier cooled plate or similar device. In an embodiment of the present invention, plate 118 is temperature-controlled such that the plate temperature can be maintained at a relatively constant temperature. However, in other embodiments of the present invention, plate temperature need be controlled as long as active cooling takes place to prevent excessive heat buildup during operation of TGA 100 at elevated temperatures. An insulated cover 103 may be provided to protect the balance chamber from atmospheric temperature fluctuations. Heaters (not shown) mounted on the balance chamber are used to control the temperature of the balance chamber.

Referring again to FIG. 1, an interactive display 119 may be provided to display the results of any experiments run using TGA 100 as well as to control operation of TGA 100.

Figure 3:
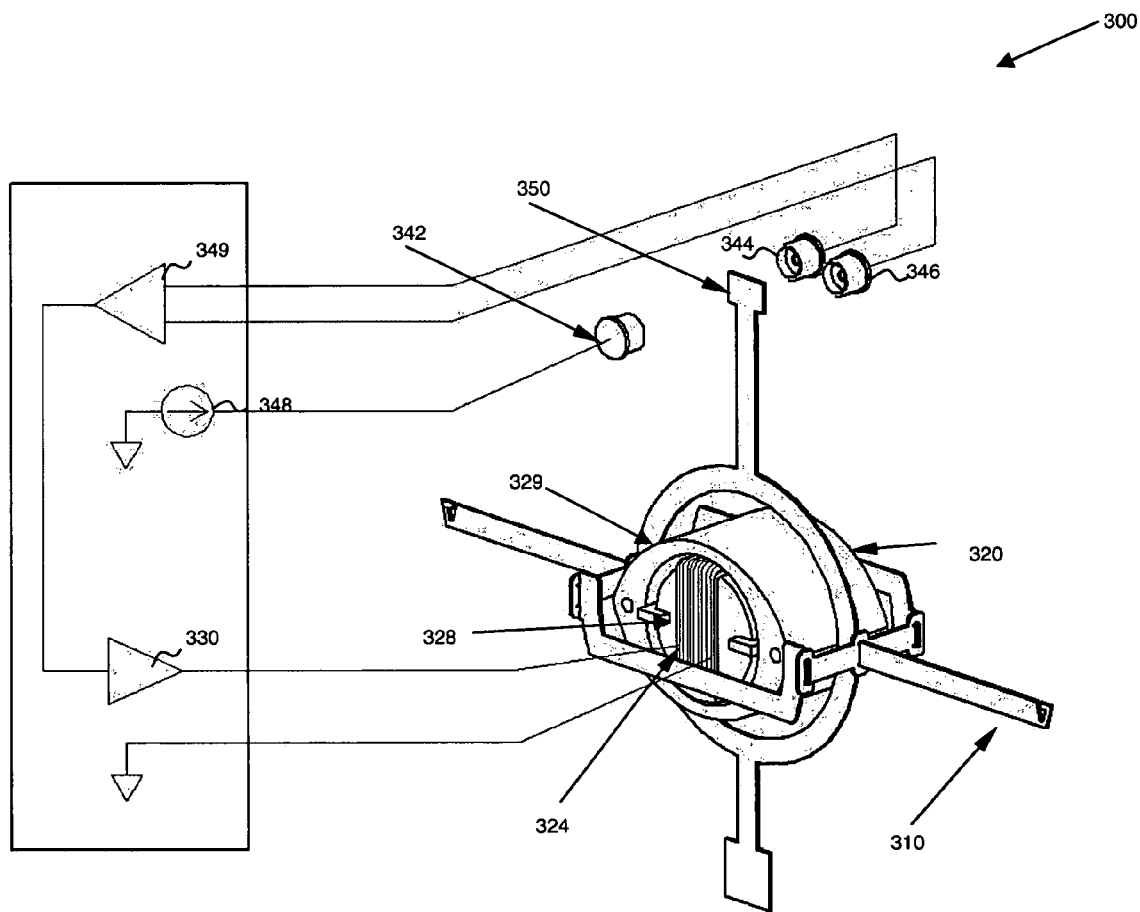
FIG. 3 is a functional block diagram showing the operation of a null balance in accordance with the exemplary embodiment of the present invention.

FIG. 3 is a schematic diagram showing null balance 300 of the present invention. Null balance 300 consists of a horizontal balance beam (also termed "balance arm" herein) 310 having attachments at its extremities for suspension of a sample pan (not shown) at one end and a tare pan (not shown) at the other end. The tare pan offsets the weight of the sample pan, thereby approximately balancing the sample pan mass and reducing the drive force required to maintain equilibrium. A meter movement 320 provides the drive force to maintain null balance 300 in the null position and supports balance beam 310.

The meter movement 320 consists of a taut band (not shown) that supports a wire coil 324 to which balance beam 310 is mounted and a field assembly comprising a permanent magnet 328 and magnetically soft iron armature 329 to create a constant strength magnetic field. Electrical current supplied by a meter coil drive 330 passes through wire coil 324 and interacts with the magnetic field to apply torque to balance beam 310 to maintain the null position. The electrical current in the coil when null balance 300 is in the null position is directly proportional to the sum of the forces acting on balance arm 310 and is a measure of the sample weight when all of the extraneous forces have been eliminated or accounted for.

Displacement of null balance 300 from the null position is sensed by a displacement sensor that consists of a light emitting diode (LED) 342, a pair of light sensing diodes 344, 346, a current source 348 to illuminate LED 342 and position error detection circuitry 349. A flag 350 attached to balance beam 310 is interposed between LED 342 and light sensing diodes 344, 346 such that flag 350 obscures a portion of the light emitted by LED 342 toward sensing diodes 344, 346. Any movement of flag 350 changes the amount of light incident upon each of sensing diodes 344, 346, increasing the energy reaching one and decreasing the energy reaching the other.

The magnitude and sense of the imbalance of energy falling on sensing diodes 344, 346 generates a position error signal that is fed to meter coil drive 330 that varies the coil current to restore null balance 300 to the null position. Thus, the meter drive coil current is proportional to the measured sample weight. To achieve optimum performance, any extraneous forces acting on null balance 300 must be eliminated or compensated, to eliminate or minimize errors in the measured weight.

Figure 4:
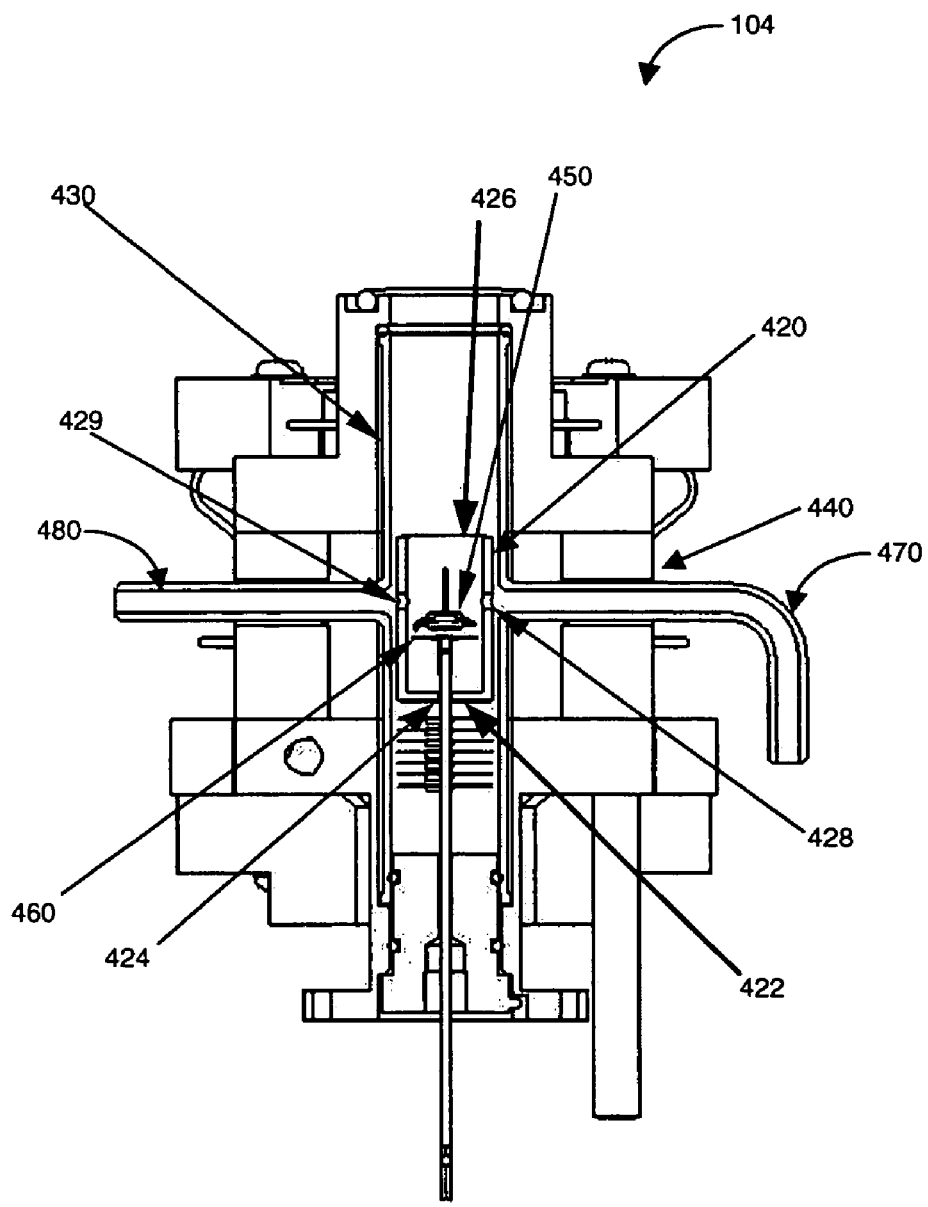
FIG. 4 is a vertical cross section through the furnace assembly of the TGA shown in FIG. 1.
Figure 5:
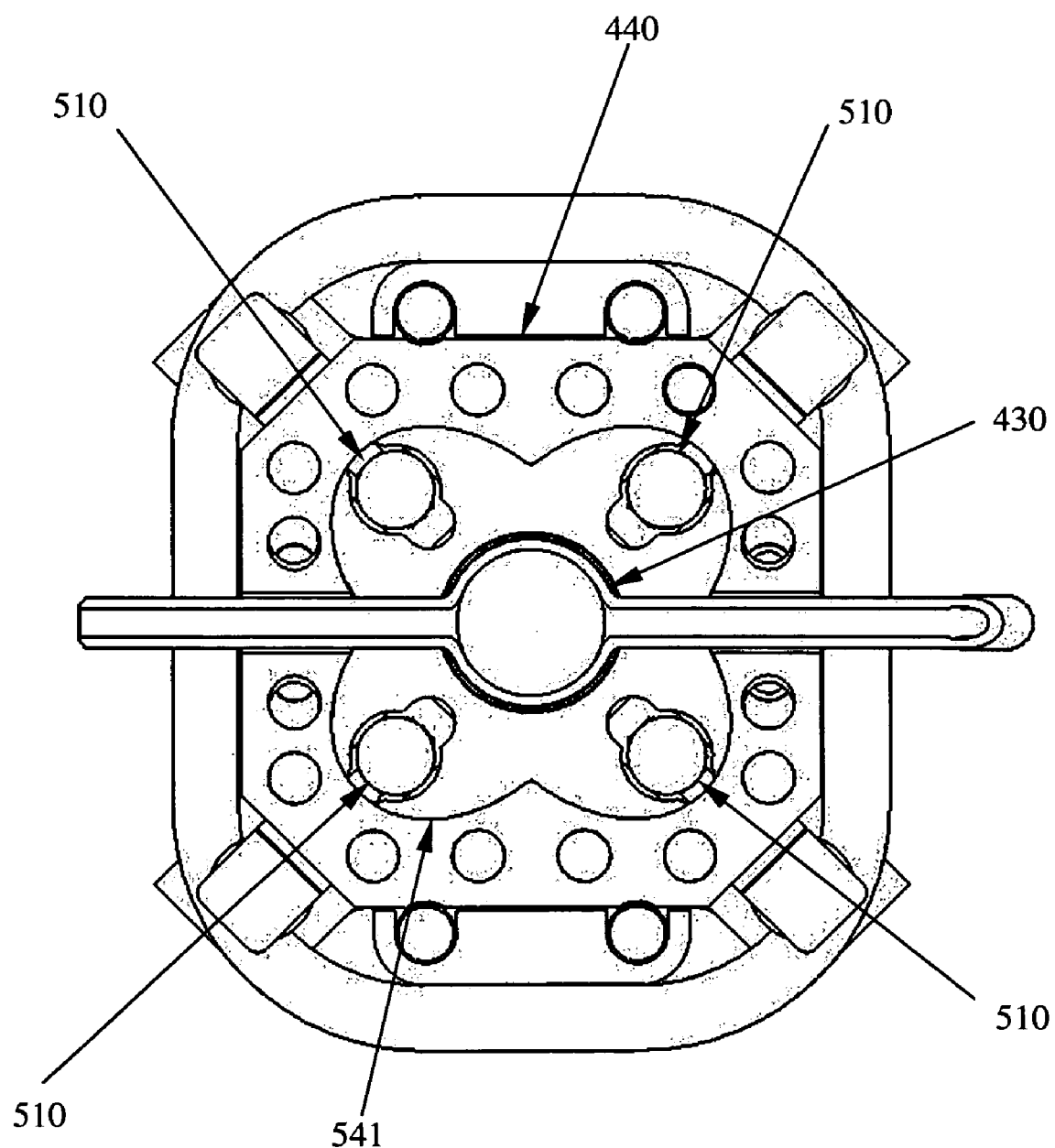
FIG. 5 is a horizontal cross section through the furnace assembly of the TGA shown in FIG. 1.

FIGS. 4 and 5 illustrate exemplary features of a preferred embodiment of the present invention, wherein furnace 104 is an infrared furnace that uses quartz halogen lamps. Four tubular quartz halogen lamps 510 (FIG. 5) irradiate a silicon carbide cylinder 420 enclosed within a quartz tube 430. Water-cooled reflector assembly 440 surrounds the four lamps 510 and quartz tube 430 to direct the radiation emitted from lamps 510 toward the outside surface of silicon carbide cylinder 420. The radiation heats silicon carbide cylinder 420, which, in turn, heats the sample (not shown), sample pan 450 and thermocouple disk 460 located within silicon carbide cylinder 420. Silicon carbide was chosen because it is capable of resisting the high temperatures encountered in a TGA, has high thermal conductivity that improves temperature uniformity and has high emissivity so that it heats efficiently. Lower end 422 of the silicon carbide cylinder is closed except for a small hole 424 for a support for thermocouple disk 460, while top end 426 of cylinder 420 is open to allow the sample pan 450 to enter furnace 104.

The temperature inside cylinder 420 is measured by a thermocouple (not shown) welded to thermocouple disk 460, which is nearly the same diameter as the inside of the silicon carbide cylinder 420 and located just below sample pan 450. This configuration leads to improved temperature uniformity that helps to reduce temperature gradients in the region of sample pan 450, which reduces gas density differences within this region and hence reduces gas circulation by natural convection that may cause weighing errors. It also restricts the effective size of furnace 104 immediately surrounding and below sample pan 450 to limit the circulation of gas resulting from density differences caused by non-uniformity of temperature within the furnace 104.

Purge gas enters furnace 104 via inlet tube 470, passes through hole 428 of the vertical wall of silicon carbide cylinder 420. The purge gas passes above the sample in sample pan 450 and exits via a second hole 429 through the vertical wall of silicon carbide cylinder 420 located diametrically opposite first hole 428. The purge gas exits furnace 104 via exit tube 480. Typical purge gases include dry air, oxygen, nitrogen, argon, helium, carbon monoxide and carbon dioxide.

Because the flow of purge gas from inlet 470 to exit 480 is orthogonal to the force of gravity, it has a minimal effect on the weight measurement. Thus it will be recognized that a furnace having this configuration will greatly reduce gas flow forces acting on sample pan 450, whether the flows are from purge gas or result from density differences due to temperature variation within the furnace.

FIG. 5 is a horizontal cross section through the furnace assembly taken at the centerline of purge gas inlet tube 470 and exit tube 480. Quartz tube 430 is located at the center of reflector 440 and is surrounded by four tubular quartz halogen lamps 510 disposed equidistant from the quartz tube and from one another. Cavity 541 of the reflector, which is the reflecting surface, is formed by the intersection of four elliptical cylinders. Each cylinder is disposed such that one of its foci is coincident with the centerline of the quartz tube and its other focus is coincident with the centerline of the lamp within that cylinder. In this fashion, the majority of the radiation emitted by the lamps is directed toward the silicon carbide cylinder at the center of the quartz tube.

Figure 6:
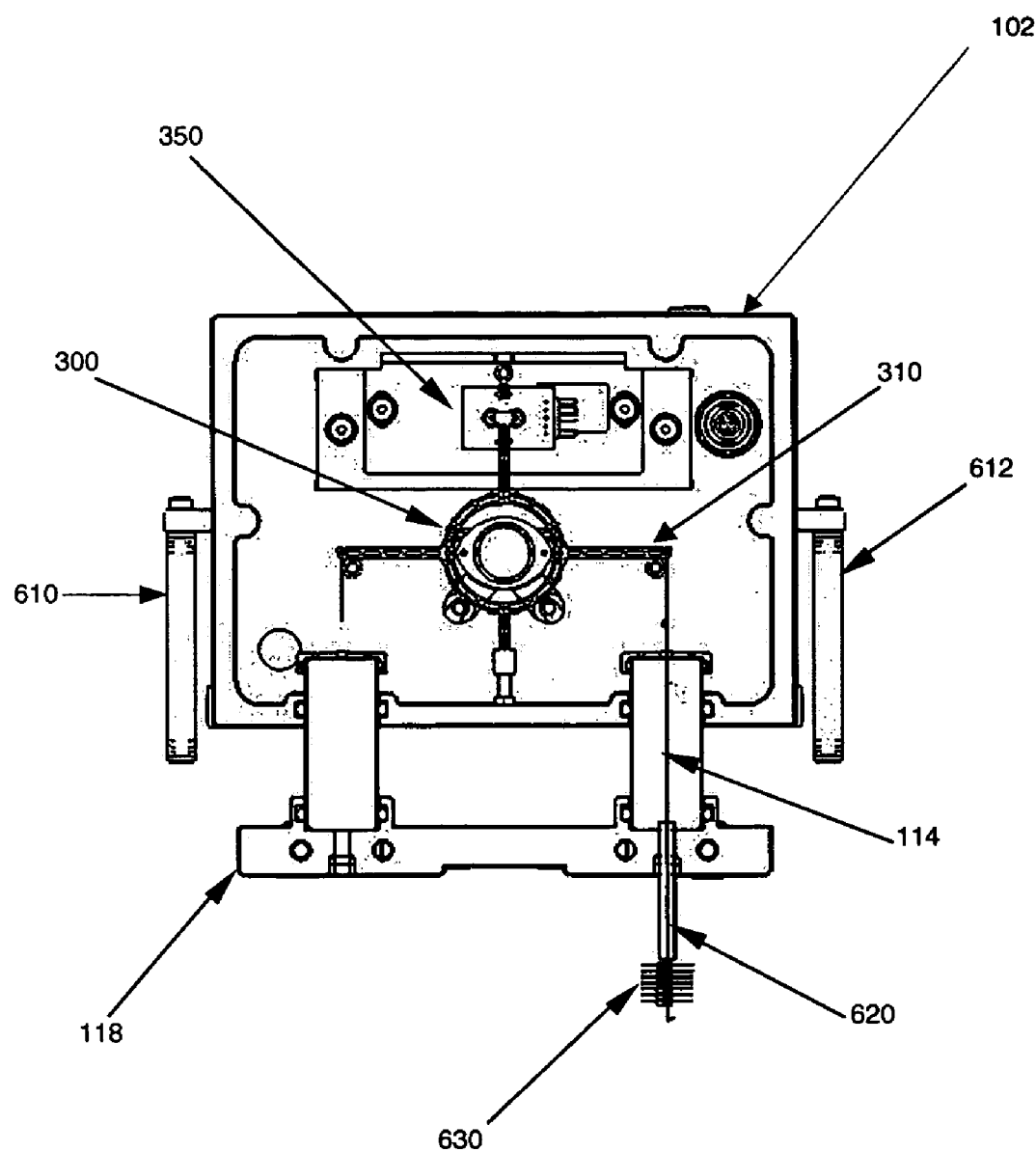
FIG. 6 is a vertical cross section through the balance chamber assembly of the TGA shown in FIG. 1.

FIG. 6 illustrates further details of a null balance chamber, according to one embodiment of the present invention, Null balance 300 with a suspension filament pan support 114 is arranged in a temperature controlled balance chamber 102, as shown in FIG. 6. As shown in FIG. 1, balance chamber 102 is mounted above furnace 104. Preferably, balance chamber 102 has its temperature precisely controlled above ambient temperature and is thermally isolated from its surroundings, in particular from furnace 104 disposed beneath it. Thermal isolation of balance chamber 102 is accomplished using thermal insulation surrounding the chamber (not shown) and structural supports 610 and 612 that have high thermal resistance while possessing high rigidity. Thermal isolation of balance chamber 102 from furnace 104 is additionally achieved by placing actively cooled plate 118 beneath balance chamber 102. Suspension filament 114 passes through water-cooled plate 118. Water-cooled plate 118 supports a thin wall metallic tube 620 and a system of heat shields 630 attached to the bottom of tube 620. Metallic tube 620 shields suspension filament 114. Water-cooled plate 118, thin metallic tube 620 and heat shields 630 are grounded to facilitate discharge of static charges.

In operation, furnace 104 is lowered to load a sample. When furnace 104 is raised to run an experiment, it closes against water-cooled plate 118. Heat shields 630 attached to thin metallic tube 620 enter furnace 104 and are located above the open end 426 of silicon carbide cylinder 420 when furnace 104 is fully raised. In this manner, balance chamber 102 is thermally isolated from furnace 104.

Null balance 300 contains a substantially small amount of hygroscopic material (such as polymeric materials and adhesives) and balance chamber 102 is purged with dry gas to reduce the magnitude of moisture adsorption. To eliminate the accumulation of static charge, balance beam 310 and suspension filament 114 are entirely made of metal and are electrically grounded by a fine gauge spring wire (not shown) so that static charges will be readily discharged to ground.

To obtain high precision weight measurements in TGA, buoyancy corrections must be applied to the measured weight. The buoyancy correction is based upon the Archimedes principle that a buoyancy force acts on an immersed body that is equal to the weight of the displaced fluid. Because the temperature of the gas within furnace 104 (and hence its density) changes during an experiment, the buoyancy force changes. Gas density decreases with increasing temperature so that the buoyancy force decreases and an apparent weight gain is observed. Two components of buoyancy force may be included, one attributable to the apparatus and the other attributable to the sample. The apparatus component has essentially constant volume, neglecting changes in volume due to thermal expansion and includes sample pan 450 and a portion of pan suspension filament 114. The sample component has variable volume due to weight loss. The buoyancy correction equations A and B are based on the ideal gas law (Eq. C) and assume that the gas pressure is constant. Thus gas density is inversely proportional to absolute gas temperature.

Apparatus Buoyancy Force Correction $$b_a = V_a \rho_t \left(1 - \frac{T_t}{T}\right) \quad [\text{Eq. A}]$$

Sample Buoyancy Force Correction $$b_s = V_i \frac{m_s}{m_i} \rho_i \left(1 - \frac{T_i}{T}\right) \quad [\text{Eq. B}]$$

Gas Density Equation (Ideal Gas Law)

$$\rho = \frac{p}{RT} \quad [\text{Eq. C}]$$

The gas density equation is used to calculate the densities used in the apparatus and sample buoyancy force equations, or tabular data may be used. The corrected weight measurement is then determined by subtracting from the measured sample weight both the apparatus and sample buoyancy factors.

Corrected Weight Measurement $$m = m_s - b_s - b_a \quad [\text{Eq. D}]$$

The following definitions are provided for the above equations:

$b_a$—apparatus buoyancy correction to the weight measurement
$V_a$—apparatus volume, that of the pan and a portion of the pan suspension filament
$\rho_t$—density of the gas when the pan weight is tared
$T_t$—absolute temperature of the gas when the pan weight is tared
$T$—absolute temperature of the gas during the experiment
$b_s$—sample buoyancy correction to the weight measurement
$V_i$—volume of the sample when the starting sample weight is measured
$m_s$—measured sample weight (initial pan mass is tared)
$m_i$—initial sample weight
$\rho_i$—density of the gas when the initial sample weight is taken
$T_i$—absolute temperature of the gas when the initial sample weight is taken
p—atmospheric pressure (assumed to be 101300 Pa)
R—specific gas constant Sample and pan buoyancy corrections are applied to the TGA weight measurement using the measured temperature to calculate the buoyancy force to be subtracted from the weight measurement. Start-up weight offsets occur because the gas in furnace 104 heats more quickly than sample pan 450, sample and thermocouple disk 460. Thus, a disproportionately large buoyancy force occurs at low temperature that is not properly compensated by the buoyancy correction. A temperature correction may be applied to the measured temperature to reduce the start-up weight gain. Assuming the temperature of the gas is close to that of silicon carbide cylinder 420 and that heat exchange between thermocouple disk 460 and cylinder 420 is predominately by diffuse-gray radiation, a simple expression for cylinder 420 and gas temperature may be used for temperature correction.

Temperature Correction $$T = \left(K_m \dot{T}_m + T_m^4\right)^{\frac{1}{4}} \quad [\text{Eq. E}]$$

The following definitions are provided for the above equation:

$T_m$—measured absolute temperature ($T_m$ with a dot indicates a time derivative, i.e., $dT_m/dt$, where t represents time)
T—cylinder absolute temperature
$K_m$—empirical heat exchange coefficient When the temperature correction is employed, the value of T calculated above is substituted for the temperature in the buoyancy correction equations; otherwise the temperature measured by the thermocouple is used without the correction.

Figure 7:
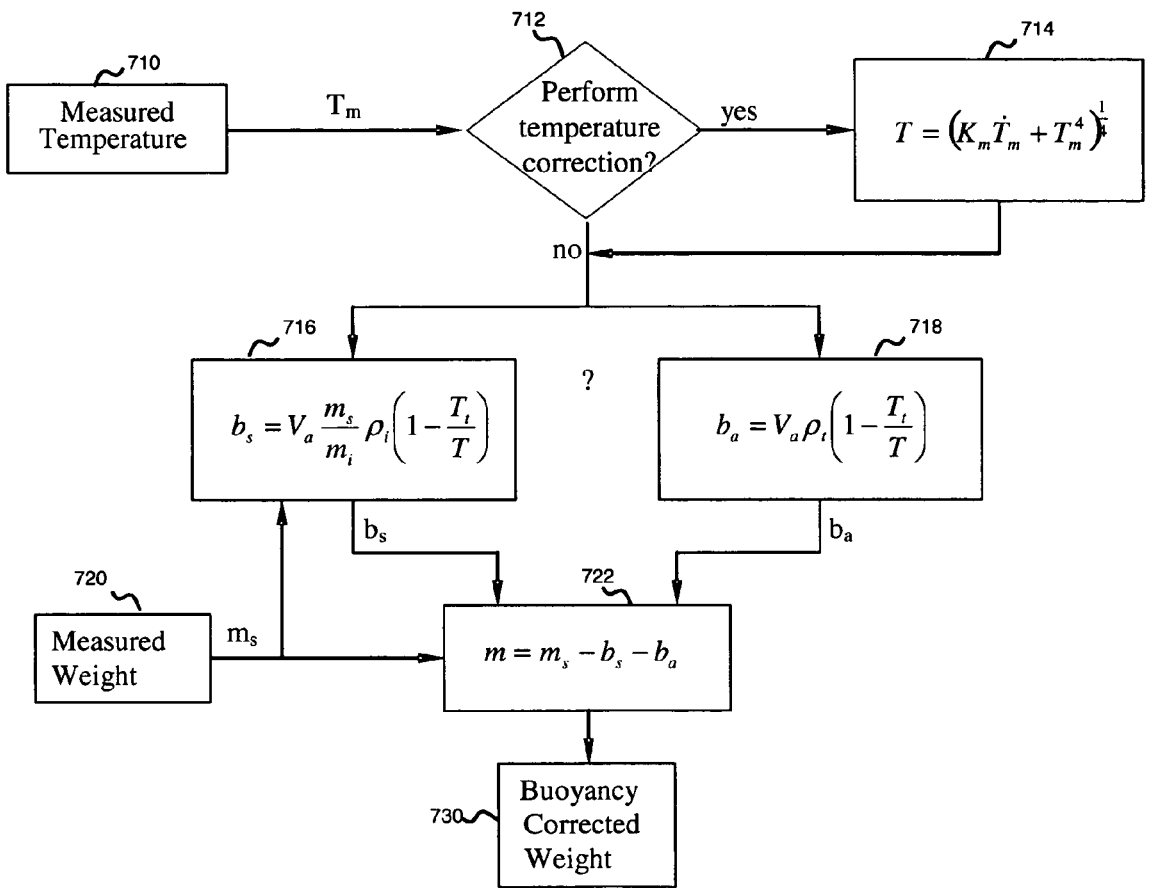
FIG. 7 is a flow chart showing a method of temperature and buoyancy correction in accordance with an exemplary embodiment of the present invention.

In preferred embodiments of the present invention, algorithms based on the above equations A-E or mathematical equivalents thereof, are performed by processor 108 in order to properly calculate sample weight and sample temperature. The term "mathematical equivalents" refers to equations or algorithms that operate to produce the same result based on given input and variables. Thus, one algorithm that is the mathematical equivalent of equation D above would be: a) summing up the buoyancy correction factors $b_a$ and $b_s$) subtracting the result from measured sample weight $m_s$ to obtain m, in other words $m=m_s-(b_s+b_a)$ FIG. 7 is a flowchart showing exemplary steps and inputs involved in a method of correcting the TGA weight measurement for buoyancy effects, according to an embodiment of the present invention. Preferably, electronic control unit 108 is configured to perform the TGA weight measurement correction steps outlined in FIG. 7. Temperature and buoyancy corrections performed in steps 714, 716, 718, and 722 are based on equations E, B, A, and D, respectively, or their mathematical equivalents. Inputs 710, 720 are the measured temperature from a thermocouple situated within the silicon carbide cylinder beneath the sample pan and the sample weight measured by the null balance, respectively. Output 730 is the measured weight corrected for buoyancy effects.

At step 712, the measured temperature $T_m$ supplied at input 710 may be left uncorrected, in which case the method moves to steps 716 and 718 described below. Alternatively, if it is determined that the measured temperature $T_m$ is to be corrected, the method moves to step 714 where the temperature correction as described above in Eq. E is applied, and subsequently the corrected temperature value is supplied as the parameter T for the buoyancy correction operations performed at steps 716 and 718.

Steps 716 and 718 receive as temperature input, either the value $T_m$ directly supplied from input 710 through step 712, or the value T, supplied from step 714. In addition to a temperature input, measured weight $m_s$ is supplied from input 720 to the sample buoyancy correction calculation performed at step 716, which, along with the gas temperature T (either calculated T from step 714 or $T_m$ from input 710), is used to calculate the sample buoyancy force $b_s$. Gas temperature T (using calculated T from step 714 or $T_m$ from input 710) is the sole input used to calculate the apparatus buoyancy correction $b_a$ at step 718.

In step 722, correction factors, if any, are applied to the measured sample weight $m_s$ to determine the corrected sample weight m. In the example depicted in FIG. 7, the sample and apparatus buoyancy forces $b_s$ and $b_a$, respectively, are subtracted from the sample weight at step 722 to give the buoyancy corrected weight m supplied as output 730. However, in other embodiments of the present invention, the user of the TGA may chose to apply $b_s$ alone, $b_a$ alone, or neither of the buoyancy corrections in determining m.

Additionally, the user may also choose on an individual sample basis as whether to apply the gas temperature correction of Eq. E. The experimental method outlined in FIG. 7 can be repeated for any number of temperature measurements and can be programmed to follow a specific temperature profile (a specific protocol including a temperature range or set of temperature ranges for sample heating, heating rate or rates corresponding to the temperature ranges, hold temperatures and hold times, if any, etc.). In this manner, a buoyancy corrected sample weight can be determined and stored as a function of temperature over any desired accessible temperature range and temperature profile.

Figure 8:
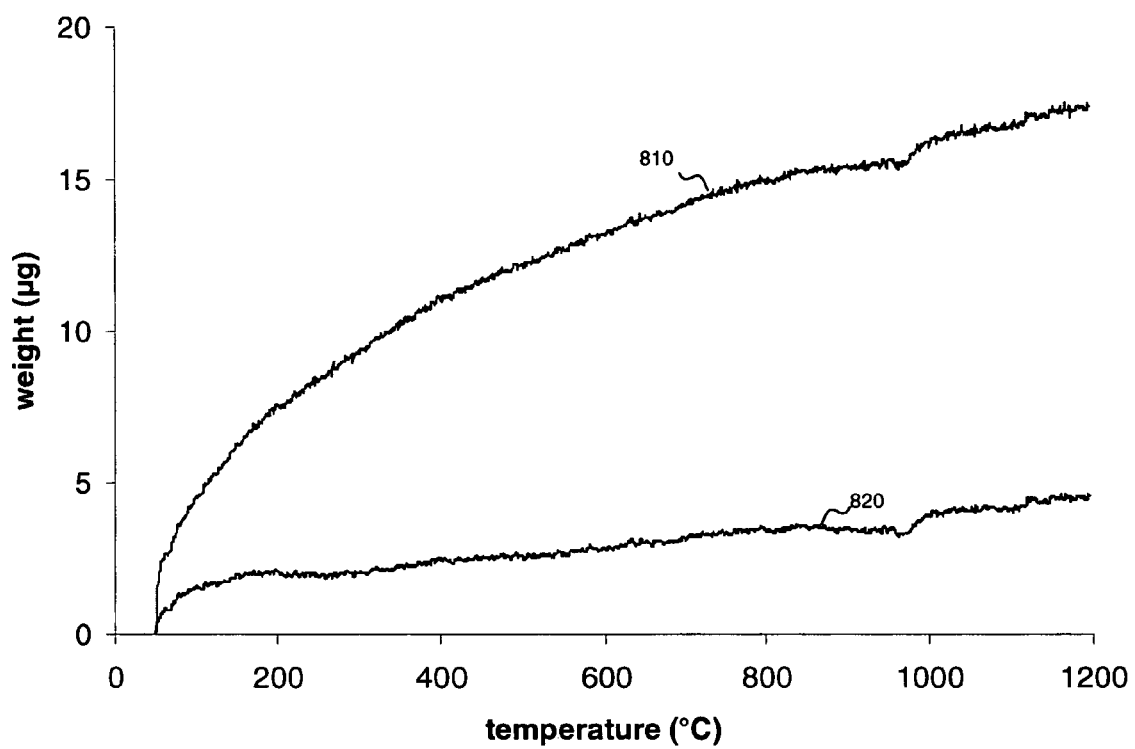
FIG. 8 is a plot of a TGA dynamic weight baseline showing the uncorrected baseline and the baseline after buoyancy and temperature measurement correction are applied in accordance with an exemplary embodiment of the present invention.
Figure 9A:
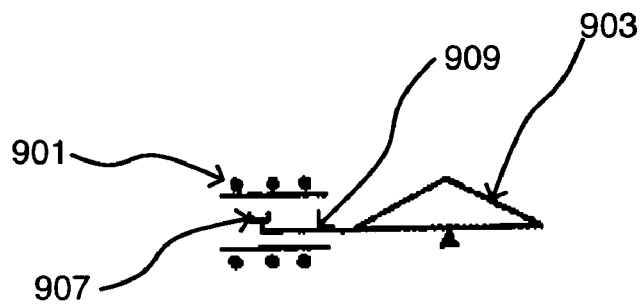
FIGS. 9A, 9B, and 9C are schematics showing various known configurations of TGAs.
Figure 9B:
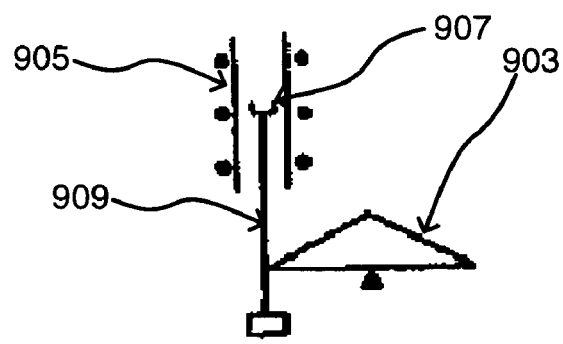
Figure 9C:
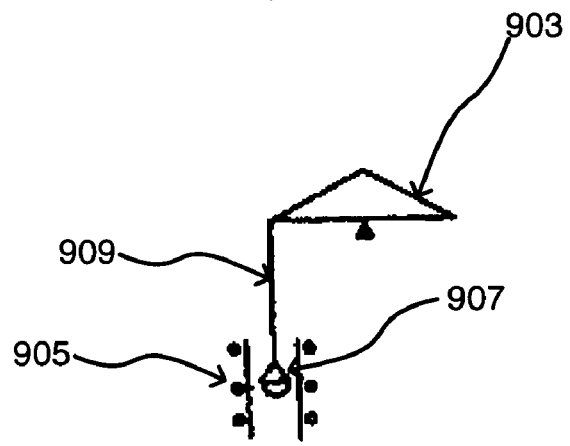

FIG. 8 shows the dynamic weight baseline result for a TGA constructed according to the present invention with and without the buoyancy correction described herein. The TGA was heated between 50° C. and 1200° C. at 20° C./min with an empty pan installed. The result labeled 810 shows the resulting weight signal in micrograms without buoyancy correction. In principle, the weight gain should be negligible during this experiment. However, there are two significant weight gains to note in curve 810. First, at the initiation of heating from the starting temperature of 50° C., the weight increases by approximately 3 μg almost immediately. This is the start-up buoyancy effect that is the result of the gas within the furnace heating faster than the pan and thermocouple. The second effect is the gradual increase in weight throughout the remainder of the experiment. Both effects are the result of reduced buoyancy force acting on the pan as the gas temperature rises. Altogether, there is an apparent weight gain of 17.4 μg. This amount of weight gain can accordingly by considered to be mostly an artifact of the TGA measurement and not any true sample weight gain. The result labeled 820 is the buoyancy corrected dynamic baseline determined according to the methods of the present invention described above. The prompt start-up weight gain is greatly reduced, while the total apparent weight gain is reduced to 4.5 μg by the application of the buoyancy correction. Thus, the vast majority of the sample weight gain artifacts are eliminated. In addition, because embodiments of the present invention serve to reduce artifacts such as balance chamber temperature fluctuations, static charge buildup, and sample furnace convection currents, each of which can cause unpredictable changes in apparent sample weight, when TGA measurements are recorded with buoyancy and temperature corrections applied, the resulting dynamically corrected curves yield much more reproducible results for any given sample. Additionally, less variation in TGA measurements is seen between measurements performed on different instruments that employ the embodiments of the present invention disclosed above.

The foregoing disclosure of an exemplary embodiment of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A thermogravimetric analyzer comprising:
   (a) a balance chamber;
   (b) a furnace containing an infrared heat source configured to heat a cylinder contained therein, the cylinder adapted to transfer heat to a sample; and
   (c) an actively cooled plate positioned between the balance chamber and the furnace, wherein the actively cooled plate is a water-cooled plate, the thermogravimetric analyzer further comprising a null balance located in the balance chamber, a filament connected to the null balance, a sample pan supported by the filament in the furnace, a thin metallic tube enclosing the filament, and a plurality of heat shields supported by the thin metallic tube and disposed between the balance chamber and the furnace.

2. The thermogravimetric analyzer of claim 1, wherein the actively cooled plate is configured to improve thermal isolation of the balance chamber by removing heat received from the furnace.

3. The thermogravimetric analyzer of claim 1, wherein the actively cooled plate is temperature-controlled.

4. The thermogravimetric analyzer according to claim 1, wherein the infrared heat source is a plurality of halogen lamps.

5. The thermogravimetric analyzer according to claim 1, further comprising:
(a) an insulated cover surrounding the balance chamber; and
(b) heaters mounted on the balance chamber, and adapted to control temperature of the balance chamber.

6. A thermogravimetric analyzer comprising:
(a) a balance configured to periodically measure sample weight over a temperature range;
(b) a furnace containing an infrared heat source configured to heat a cylinder contained therein, the cylinder adapted to transfer heat to a sample;
(c) a pan supporting the sample;
(d) a filament connecting the pan to the balance, the pan and a portion of the filament being located within the cylinder; and
(e) a thermocouple located inside the cylinder, the thermocouple being welded to a disk of substantially the same diameter as an inner diameter of the cylinder and arranged beneath the pan such that the disk restricts circulation of gas caused by differences of temperature within the cylinder
(f) a chamber located above the furnace, wherein the balance is located inside the chamber and is thermally isolated from the furnace; and
(g) an actively cooled plate located beneath the chamber, wherein the actively cooled plate thermally isolates the chamber from the furnace, and wherein the actively cooled plate is cooled by water.

7. The thermogravimetric analyzer according to claim 6, further comprising a computer configured to calculate a correction factor to be applied to the sample weight measured by the balance over the temperature range.

8. The thermogravimetric analyzer according to claim 6, wherein the balance is located above the furnace.

9. The thermogravimetric analyzer according to claim 8, wherein the balance is a null balance.

10. The thermogravimetric analyzer according to claim 9, wherein the null balance comprises a balance arm configured to support the pan, a drive system configured to apply force to the balance arm, a displacement sensor configured to detect displacement of the balance arm, and control means configured to operate the drive system to keep the balance arm in equilibrium.

11. The thermogravimetric analyzer according to claim 10, wherein the computer receives an output from the drive system measuring the force applied by the drive system to keep the balance arm in equilibrium and the computer converts the output to a measured weight of the sample.

12. The thermogravimetric analyzer according to claim 6, wherein the cylinder includes a first hole configured to allow transmission of a purge gas into the cylinder and a second hole configured to allow transmission of the purge gas out of the cylinder.

13. The thermogravimetric analyzer according to claim 12, wherein each hole is located on a vertical wall of the cylinder.

14. The thermogravimetric analyzer according to claim 6, wherein the actively cooled plate is temperature-controlled.

15. The thermogravimetric analyzer according to claim 6, the balance comprising a metallic balance arm the filament comprising a metallic material, the balance arm and filament electrically grounded by a wire.

16. A thermogravimetric analyzer comprising:
(a) a balance;
(b) a pan for supporting a sample;
(c) a filament connecting the pan to the balance;
(d) a furnace to heat the sample;
(e) a thin metallic tube surrounding the filament and having attached heat shields; and
(f) means for calculating a corrected weight (m) including means for measuring a weight of the sample ($m_s$) and means for calculating a buoyancy factor, the means for calculating a buoyancy factor including calculating a buoyancy factor for the sample ($b_s$) according to:

$$b_s = V_i \frac{m_s}{m_i} \rho_i \left(1 - \frac{T_i}{T}\right)$$

or a mathematical equivalent, wherein $m_i$ is an initial weight of the sample, $\rho_i$ is gas density when the initial weight of the sample is measured, $T_i$ is absolute temperature of the gas when the initial weight of the sample is measured, $V_i$ is volume of the sample when the initial weight of the sample is measured, and T is absolute temperature of the gas during the experiment.

17. The thermogravimetric analyzer according to claim 16, wherein the means for calculating the corrected weight m includes calculating the corrected weight according to:

$m = m_s - b_s$ or a mathematical equivalent.

18. The thermogravimetric analyzer according to claim 16, wherein the means for calculating the buoyancy factor includes calculating a buoyancy factor for the pan and filament ($b_a$) according to:

$$b_a = V_a \rho_t \left(1 - \frac{T_t}{T}\right)$$

or a mathematical equivalent, wherein $V_a$ is apparatus volume, that of the pan and a portion of a pan suspension filament, $\rho_t$ is gas density when a pan weight is tared, and $T_t$ is absolute gas temperature when the pan weight is tared.

19. The thermogravimetric analyzer according to claim 18, wherein the means for calculating the corrected weight includes calculating the corrected weight according to:

$m = m_s - b_s - b_a$ or a mathematical equivalent.

20. The thermogravimetric analyzer according to claim 16, wherein the furnace is a vertical furnace.

21. The thermogravimetric analyzer according to claim 16, wherein the balance is a null balance.

22. The thermogravimetric analyzer according to claim 21, wherein the null balance comprises a balance arm configured to support the pan, a drive system configured to apply force to the balance arm, a displacement sensor configured to detect displacement of the balance arm, and control means configured to operate the drive system to keep the balance arm in equilibrium.

23. The thermogravimetric analyzer according to claim 22, wherein the means for measuring the weight of the sample comprises measuring the force applied by the drive system to keep the balance arm in equilibrium.

24. A method for calculating a weight of a sample in a thermogravimetric analyzer comprising a balance, a pan for supporting a sample, a filament connecting the pan to the balance, a furnace to heat the sample, and an actively cooled plate located between the balance chamber and the furnace, the method comprising:
   (a) the step of measuring the weight of the sample in $m_s$;
   (b) the step of calculating a buoyancy factor, including calculating a buoyancy factor for the sample ($b_s$) according to:

$$b_s = V_i \frac{m_s}{m_i} \rho_i \left(1 - \frac{T_i}{T}\right)$$

or a mathematical equivalent; and
   (c) the step of calculating a corrected weight m based on the buoyancy factor, wherein $m_i$ is an initial weight of the sample, $\rho_i$ is gas density when the initial weight of the sample is measured, $T_i$ is absolute temperature of the gas when the initial weight of the sample is measured, $V_i$ is volume of the sample when the initial weight of the sample is measured, and T is absolute temperature of the gas during the experiment.

25. The method according to claim 24, wherein step (c) comprises calculating the corrected weight based on the buoyancy factor according to:

$m=m_s-b_s$ or a mathematical equivalent.

26. The method according to claim 24, wherein step (b) further comprises calculating a buoyancy factor for the pan and filament ($b_a$) according to:

$$b_a = V_a \rho_t \left(1 - \frac{T_t}{T}\right)$$

or a mathematical equivalent, wherein $V_a$ is apparatus volume, that of the pan and a portion of a pan suspension filament, $\rho_t$ is gas density when a pan weight is tared, and $T_t$ is absolute gas temperature when the pan weight is tared.

27. The method according to claim 26, wherein step (c) comprises calculating the corrected weight based on the buoyancy factor according to:

$m=m_s-b_s-b_a$ or a mathematical equivalent.

28. The method according to claim 24, wherein step (b) further comprises compensating for low temperature at start-up by substituting for T based on a measured temperature $T_m$ according to:

$$T = \left(K_m \dot{T}_m + T_m^4\right)^{\frac{1}{4}}$$

or a mathematical equivalent, wherein $K_m$ is an empirical heat exchange coefficient.

29. The method according to claim 26, wherein step (b) comprises calculating the buoyancy factor further comprises compensating for low temperature at start-up by substituting for T based on a measured temperature $T_m$ according to:

$$T = \left(K_m \dot{T}_m + T_m^4\right)^{\frac{1}{4}}$$

or a mathematical equivalent, wherein $K_m$ is an empirical heat exchange coefficient.

30. The method according to claim 27, wherein step (b) further comprises compensating for low temperature at start-up by substituting for T based on a measured temperature $T_m$ according to:

$$T = \left(K_m \dot{T}_m + T_m^4\right)^{\frac{1}{4}}$$

wherein $K_m$ is an empirical heat exchange coefficient.

31. The method according to claim 24, wherein the furnace is a vertical furnace.

32. The method according to claim 24, wherein the balance is a null balance.

33. The method according to claim 32, wherein the null balance comprises a balance arm configured to support the pan, a drive system configured to apply force to the balance arm, a displacement sensor configured to detect displacement of the balance arm, and control means configured to operate the drive system to keep the balance arm in equilibrium.

34. The method according to claim 33, wherein step (a) comprises measuring the force applied by the drive system to keep the balance arm in equilibrium.

35. A method for calculating a weight of a sample in a thermogravimetric analyzer comprising a balance chamber for housing a balance, a furnace arranged beneath the balance chamber to heat the sample, a pan for supporting a sample in the furnace, a filament connecting the pan to the balance, and a thin tube surrounding the filament and having attached heat shields, the method comprising:
   (a) measuring a weight $m_s$ of the sample at a predetermined temperature;
   (b) calculating a buoyancy factor for the pan and filament ($b_a$) based on the predetermined temperature and calculating a buoyancy factor for the sample ($b_s$) based on the predetermined temperature according to:

$$b_a = V_a \rho_t \left(1 - \frac{T_t}{T}\right)$$

or a mathematical equivalent, and $$b_s = V_i \frac{m_s}{m_i} \rho_i \left(1 - \frac{T_i}{T}\right)$$

or a mathematical equivalent; and
   (c) calculating a corrected weight (m) according to:
      $m=m_s-b_s-b_a$ or a mathematical equivalent, wherein $V_a$ is apparatus volume, that of the pan and a portion of a pan suspension filament, $\rho_t$ is gas density when a pan weight is tared, and $T_t$ is absolute gas temperature when the pan weight is tared, wherein $m_i$ is an initial weight of the sample, $\rho_i$ is gas density when the initial weight of the sample is measured, $T_i$ is absolute temperature of the gas when the initial weight of the sample is measured, $V_i$ is volume of the sample when the initial weight of the sample is measured, and T is absolute temperature of the gas during the experiment.

36. The method according to claim 35, wherein step (b) comprises compensating for low temperature at start-up by substituting for T based on a measured temperature $T_m$ in the equations for ($b_a$) and ($b_s$) according to:

$$T = (K_m \dot{T}_m + T_m^4)^{\frac{1}{4}}$$

or a mathematical equivalent, wherein $K_m$ is an empirical heat exchange coefficient.

37. The method according to claim 35, wherein the balance includes a balance arm configured to support the pan, a drive system configured to apply force to the balance arm, a displacement sensor configured to detect displacement of the balance arm, and control means configured to operate the drive system to keep the balance arm in equilibrium, wherein step (a) comprises measuring the force applied by the drive system to keep the balance arm in equilibrium to determine the weight of the sample at the predetermined temperature.

38. The method according to claim 35, further comprising purging the balance chamber with a dry gas.

* * * * *